(12) United States Patent
Gerder-Kallisch et al.

(10) Patent No.: US 8,355,899 B2
(45) Date of Patent: Jan. 15, 2013

(54) ANESTHESIA APPARATUS OR RESPIRATOR WITH INTEGRATED SIMULATION FUNCTIONALITY

(75) Inventors: Ulrike Gerder-Kallisch, Lübeck (DE); Thomas Krüger, Reinfeld (DE); Thomas Peyn, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 2412 days.

(21) Appl. No.: 11/243,584

(22) Filed: Oct. 5, 2005

(65) Prior Publication Data

US 2006/0118110 A1 Jun. 8, 2006

(30) Foreign Application Priority Data

Dec. 3, 2004 (DE) .......................... 10 2004 058 264

(51) Int. Cl.
*G06G 7/58* (2006.01)
(52) U.S. Cl. .......................................................... 703/11
(58) Field of Classification Search ...................... 703/11
See application file for complete search history.

(56) References Cited

U.S. PATENT DOCUMENTS 4,917,080 A    4/1990   Bayerlein

FOREIGN PATENT DOCUMENTS

NL      8801323       12/1989
WO   WO 99/47200     9/1999

OTHER PUBLICATIONS

Mesic et al. "Computer Controlled Mechanical Simulation of the Artificially Ventilated Human Respiratory System," IEEE Transactions on Biomedical Engineering (Jun. 2003) vol. 50, No. 6, pp. 731-743.*

* cited by examiner

*Primary Examiner* — Jerry Lin
(74) *Attorney, Agent, or Firm* — McGlew and Tuttle, P.C.

(57) ABSTRACT

An anesthesia apparatus or respirator (1) enables the user (21) to simulate functions of the device and to carry out suitable operating steps depending on the situation, the device interactively responding to interventions by the user. The anesthesia apparatus or respirator (1) is equipped with at least one control and regulating unit (6), with at least one associated actuator (7, 8) and with internal and/or external sensors (9, 10) as well as with an interface unit (15) with an associated input and output unit (2, 3), respectively, for the operation, data input and output, and with an external data interface (4), wherein simulation components (12, 13) simulating the properties of the internal and/or external sensors (9, 10) with an associated simulation control (14) are present, so that the control and regulating unit (6) uses data of the simulation components (12, 13) for controlling the at least one actuator (7, 8) via the input and output unit (2, 3) and via the simulation control (14).

18 Claims, 1 Drawing Sheet

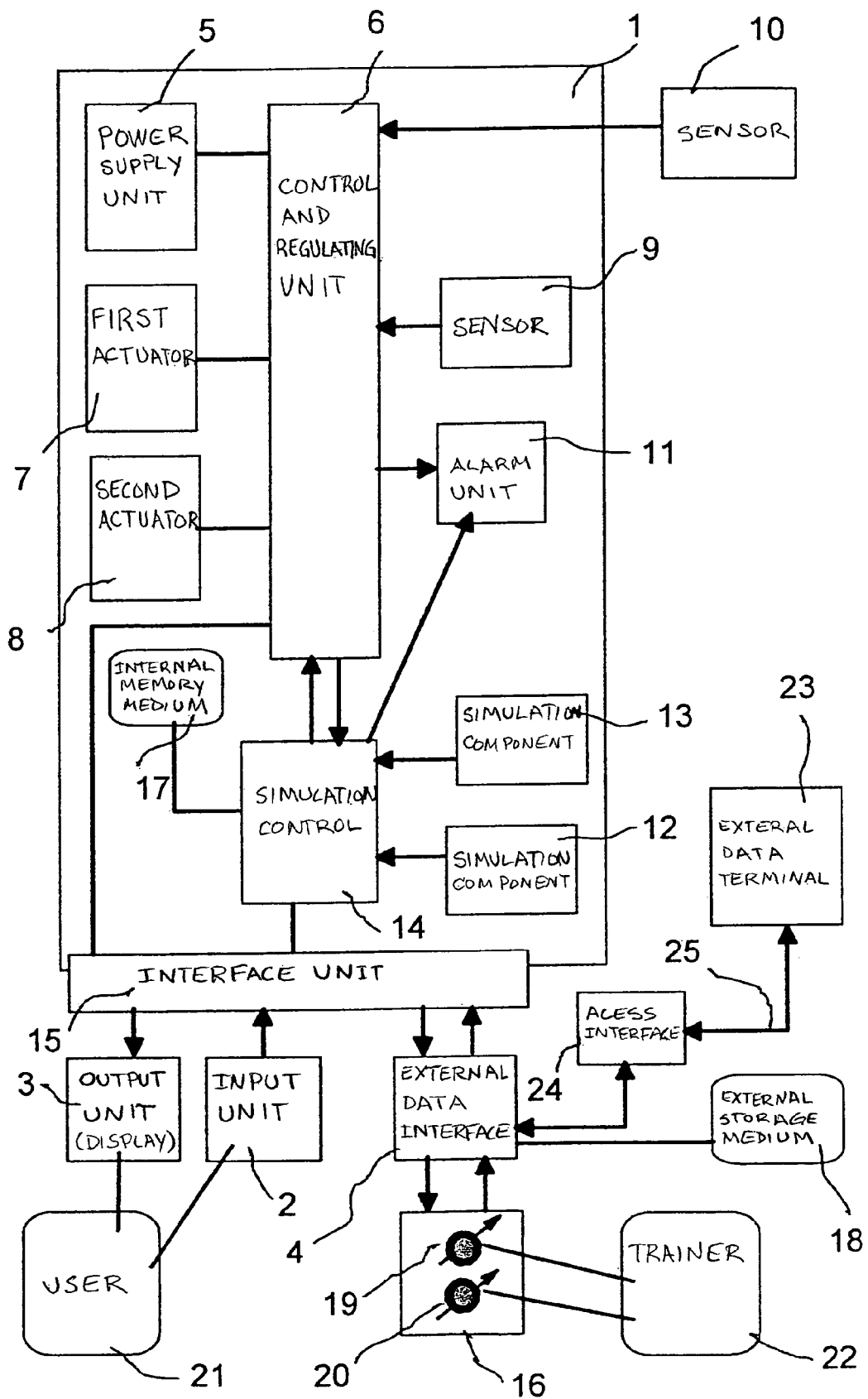

ANESTHESIA APPARATUS OR RESPIRATOR WITH INTEGRATED SIMULATION FUNCTIONALITY

CROSS REFERENCE TO RELATED APPLICATIONS

This application claims the benefit of priority under 35 U.S.C. §119 of German Application DE 10 2004 058 264.5 filed Dec. 3, 2005, the entire contents of which are incorporated herein by reference.

FIELD OF THE INVENTION

The present invention pertains to an anesthesia apparatus or respirator.

BACKGROUND OF THE INVENTION

A device used in the area of medical technology, especially an anesthesia apparatus or respirator, has various functional components, which are linked with one another such that it is possible for the user to set the apparatus and to output data specific of the operation and to activate alarms if needed. It is necessary for the user to exhaust the possibilities of such a complex device used in medical technology as optimally as possible depending on the situation in the interest of the patient being treated.

SUMMARY OF THE INVENTION

Correspondingly, the object of the present invention is to provide an anesthesia apparatus or respirator that also enables the user to simulate functions of the device and to carry out suitable operating steps depending on the situation, the device interactively giving feedback to the interventions performed by the user.

According to the invention, an anesthesia apparatus or respirator is provided with at least one control and regulating unit, with at least one associated actuator and with internal and/or external sensors. The anesthesia apparatus or respirator also has an interface unit with an associated input and output unit (2, 3), respectively, for the operation, data input and output and with an external data interface. Simulation components are provided for simulating the properties of the internal and/or external sensors with an associated simulation control, so that the control and regulating unit uses data of the simulation components for controlling the at least one actuator via the input and output unit and via the simulation control.

An essential advantage of the anesthesia apparatus or respirator according to the invention is that the device is directly integrated in the simulation process, so that the functionalities of the device are not limited in any way.

Besides the output unit, an acoustic and/or optical alarm unit may be present, which is activated by the control and regulating unit or by the simulation control when actual values exceed or fall below preset limit values for the internal and/or external sensors. Depending on the data output via the output unit and/or the activation of the alarm unit and depending on the subsequent input into the input unit in the simulation control, it may be checked on the basis of preset, stored patterns whether the input in response to the preceding data output via the output unit and/or the activation of the alarm unit agrees with the pattern, the alarm unit being activated in case of disagreement.

The external data interface may be connected at the interface unit to a settable simulation component for a patient, so that the simulation control is actuated depending on the simulation parameters set for the patient. The first simulation parameter may be the resistance and the second simulation parameter may be the compliance. The first actuator may be a respiration drive and the second actuator may be an anesthetic or drug dispensing means. Simulation curves may be sent by the simulation component from an internal storage medium of the device or from an external storage medium. A logging of the simulation may be performed by means of an external access interface with a remote data connection and a data terminal. The simulation components may be embodied programmed as software.

An exemplary embodiment of the present invention will be explained below on the basis of the only FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawings:

The only FIGURE is a schematic view showing the principal components of the invention in their interaction.

DESCRIPTION OF THE PREFERRED EMBODIMENT

Referring to the drawings in particular, an anesthesia apparatus or respirator 1 contains various components, which are linked with one another such that a defined function of the device is guaranteed via an interface unit 15 with an input and output unit 2 and 3, respectively, for input by the user 21 and for the output and display of the settings of the device and status reports. Furthermore, an external communication by means of an external data interface 4 is present. One component of the device usually is a power supply unit 5 as well as at least one control and regulating unit 6. Furthermore, active electric and pneumatic components are present, for example, a first actuator 7 in the form of a respiration drive, for example, a piston drive or a radial flow compressor, and a second actuator 8 in the form of an anesthetic or drug dispensing means.

Another group of components comprises internal and/or external sensors 9, 10, for example, from the group of the pressure sensors, gas volume flow sensors or optical gas analyzers, which supply both input variables for the control and regulating unit 6 and are used for monitoring the functions and status and display functional and status data for the user 21 via the display unit 3 with a graphic or alphanumeric display.

The operating state of the device, for example, in respect to the settings of the device and current measured values sent by sensors can be documented via the external data interface 4 and stored on an external storage medium 18. In the error-free case, the cooperation of the device is obtained by correctly operating sensors 9, 10, at least one actuator 7 or 8 and the device settings selected individually for the particular patient. The user 21 receives corresponding signals or information for a non-error-free case by means of the output unit 3 and the alarm unit 11. If, for example, there is an error in the connection between the patient and the device, the user 21 can then find out the situation, eliminate it or, in case of a reaction on the part of the patient, he can respond by changing the parameters set on the device via the input unit 2. Consequently, the user 21 has essentially responded so far to error displays of the device, but it has hardly been possible so far to display and to practice the reaction to errors, the search for the error and the selection of suitable measures for eliminating the error. This becomes possible with the present device due to the presence, in addition to the real partial components, especially the sensors 9, 10, of simulation components 12, 13 with a simulation control 14, which make it possible, as desired, to design the behavior of the anesthesia apparatus or respirator such that it is also possible to simulate cases of error. The simulation components 12, 13 are preferably embodied as software programmed in the device. The central control and regulating unit 6 obtains the current data for this from the simulation components 12, 13 into the evaluating unit, after corresponding data input by the user 21, as desired, rather than from the sensors 9, 10, and it then controls the actuator or actuators 7, 8, the alarm unit 11, the output unit 3 and the data output on the basis of these data via the external data interface 4. The user 21 responds to the alarm and the data output via the display unit 3 by a corresponding input for defense against the error via the input unit 2. The simulated cause of error and the defense against error are combined in the device in the simulation control 14 and this combination makes possible the data output via the output unit 3 and the alarming of the user 21 via the alarm unit 11, so that it becomes clear whether or not the errors occurring were eliminated by the measures taken.

To make it also possible to visualize the patient's behavior and his reactions to the settings of the device, it is useful to include in the device, in addition to the simulation components 12, 13 for the sensor system, an active, settable simulation component 16, which has the properties of the patient, and whose function is to respond to the variation of set parameters with a corresponding behavior.

This settable simulation component 16 simulates, for example, especially an active lung model, so that, for example, a first simulation parameter 19, corresponding to the resistance of the lung, and a second simulation parameter 20, corresponding to the compliance of the lung, can be set by a trainer 22.

The set values are transmitted to the device via data connection via the external data interface 4. The goal of the practice in this case is to set the suitable respiration parameters such that an operation suitable for the patient is guaranteed.

The external data interface 4 is used in an expanded variant of the device to program the settable simulation component 16 with set values. Error scenarios can thus be stored in an internal memory medium 17 of the device or they are transferred from an external storage medium 18 onto this internal storage medium. In addition, it is possible to log the error scenarios, combined with the user's behavior, via the external data interface 4. The logging may be carried out synchronously in time or with an offset in time to an external data terminal 23 by means of the remote data connection 25, for example, via the internet, via the access interface 24. The ability of the anesthesia apparatus or respirator 1 to be used is guaranteed by the fact that the switch over between training or simulation operation can take place preferably only in the standby operation with clearing by corresponding data input by the user 21. The switch over into the mission operation can take place automatically by the central control and regulating unit 6 of the device, i.e., the training mode is abandoned as soon as a measured value shows an appreciable change. As an option, manual switch over from the training mode is possible at any time.

While a specific embodiment of the invention has been shown and described in detail to illustrate the application of the principles of the invention, it will be understood that the invention may be embodied otherwise without departing from such principles.

What is claimed is:

1. An anesthesia apparatus or respirator, comprising:
   a control and regulating unit with an associated actuator;
   internal and/or external sensors;
   an interface unit with an associated input and output unit, respectively, for an operation, data input and output and with an external data interface;
   a simulation control; and
   simulation components simulating the properties of the internal and/or external sensors, said simulation components being associated with said simulation control and simulating characteristics of the sensors including providing sensor simulation parameters with an assigned simulation control to the control and regulating unit, the control and regulating unit using data of the simulation components including using said sensor simulation parameters for using the simulation components instead of the sensors for controlling the actuator via the input and output unit and via the simulation control.

2. An anesthesia apparatus or respirator in accordance with claim 1, wherein besides the output unit, an acoustic and/or optical alarm unit is provided, which is activated by the control and regulating unit or by the simulation control when actual values or said simulation parameters of the internal and/or external sensors exceed or fall below preset limit values for the internal and/or external sensors.

3. An anesthesia apparatus or respirator in accordance with claim 1, wherein depending on data output via the output unit and/or the activation of the alarm unit and depending on the subsequent input into the input unit in the simulation control, a check is made on the basis of preset, stored patterns whether the input in response to the preceding data output via the output unit and/or the activation of the alarm unit agrees with the pattern, the alarm unit being activated in case of disagreement.

4. An anesthesia apparatus or respirator in accordance with claim 1, wherein the external data interface is connected at the interface unit to a settable simulation component for a patient, so that the simulation control is actuated depending on patient simulation parameters set for the patient.

5. An anesthesia apparatus or respirator in accordance with claim 4, wherein the first patient simulation parameter is the resistance of the lung and the second patient simulation parameter is the compliance of the lung.

6. An anesthesia apparatus or respirator in accordance with claim 1, wherein the actuator comprises a first actuator in the form of a respiration drive and a second actuator in the form of an anesthetic or drug dispensing means.

7. An anesthesia apparatus or respirator in accordance with claim 4, wherein simulation curves are sent by the simulation component from an internal storage medium of the device or from an external storage medium.

8. An anesthesia apparatus or respirator in accordance with claim 1, wherein a logging of the simulation is performed by means of an external access interface with a remote data connection and a data terminal.

9. An anesthesia apparatus or respirator in accordance with claim 1, wherein the simulation components are embodied as programmed software.

10. An anesthesia or respirator system, comprising:
a control and regulating unit;
an actuator controlled by said control and regulating unit;
sensors;
a simulation control;
an input and an output unit associated with an interface unit providing an interface between the input and output unit and the control and regulating unit and the simulation control, for the operation of the system, for data input and for data output; and
simulation components simulating the properties of the sensors, said simulation components being associated with said simulation control and providing sensor simulation parameters with an assigned simulation control to the control and regulating unit, the control and regulating unit using the simulation components instead of the sensors for the control of the actuator including using data of the simulation components including using said sensor simulation parameters for controlling the actuator via the input and output unit and via the simulation control, wherein besides the output unit, an acoustic and/or optical alarm unit is provided, which is activated by the control and regulating unit or by the simulation control when actual values or said simulation parameters of the sensors exceed or fall below preset limit values for the sensors and wherein said simulation parameters include data for simulating a sensor fault or sensor failure.

11. An anesthesia apparatus or respirator in accordance with claim 10, wherein depending on data output via the output unit and/or the activation of the alarm unit and depending on the subsequent input into the input unit in the simulation control, a check is made on the basis of preset, stored patterns whether the input in response to the preceding data output via the output unit and/or the activation of the alarm unit agrees with the pattern, the alarm unit being activated in case of disagreement.

12. An anesthesia apparatus or respirator in accordance with claim 10, further comprising an external data interface wherein the external data interface is connected at the interface unit to a settable simulation component for a patient, so that the simulation control is actuated depending on patient simulation parameters set for the patient.

13. An anesthesia apparatus or respirator in accordance with claim 12, wherein the first patient simulation parameter is the resistance of the lung and the second patient simulation parameter is the compliance of the lung.

14. An anesthesia apparatus or respirator in accordance with claim 10, wherein the actuator comprises a first actuator in the form of a respiration drive and a second actuator in the form of an anesthetic or drug dispensing means.

15. An anesthesia apparatus or respirator in accordance with claim 12, wherein simulation curves are sent by the simulation component from an internal storage medium of the device or from an external storage medium.

16. An anesthesia apparatus or respirator in accordance with claim 10, wherein a logging of the simulation is performed by means of an external access interface with a remote data connection and a data terminal.

17. An anesthesia apparatus or respirator in accordance with claim 10, wherein the simulation components are embodied as a software program.

18. A method of operating an anesthesia or respirator system, comprising:
providing a control and regulating unit;
providing an actuator;
providing sensors;
providing a simulation control;
providing an input and an output unit with an associated interface unit forming an interface between the input and output unit and the control and regulating unit and the simulation control, for the operation of the system, for data input and for output;
providing simulation components;
operating the system for normal use based on data input and output to control the actuator via the control and regulating unit;
simulating operation by simulating the properties of the sensors with the simulation components being associated with the simulation control and providing simulation parameters with an assigned simulation control to the control and regulating unit, the control and regulating unit using data of the simulation components including said simulation parameters for controlling the actuator via the input and output unit and via the simulation control;
providing an acoustic and/or optical alarm unit, which is activated by the control and regulating unit or by the simulation control when actual values or said simulation parameters of the sensors exceed or fall below preset limit values for the sensors and wherein said simulation parameters include data for simulating a sensor fault or sensor failure; and
depending on data output via the output unit and/or the activation of the alarm unit and depending on a subsequent input into the input unit in the simulation control, making a check on the basis of preset, stored patterns whether the input in response to the preceding data output via the output unit and/or the activation of the alarm unit agrees with the pattern, the alarm unit being activated in case of disagreement.

* * * * *